March 24, 1959 E. J. GILBERT Plant Pat. 1,822
APPLE TREES
Filed March 5, 1958
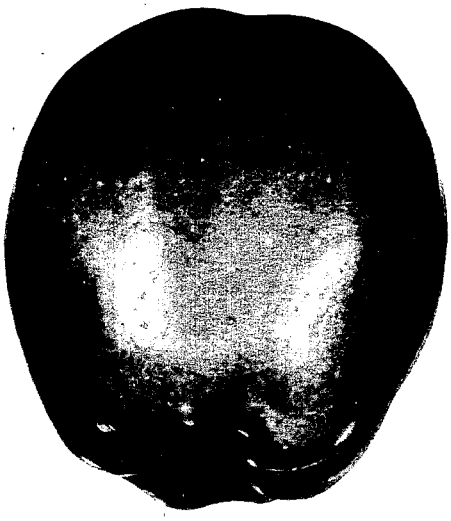
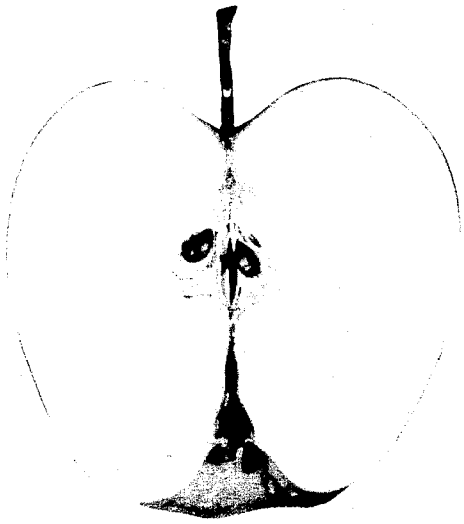
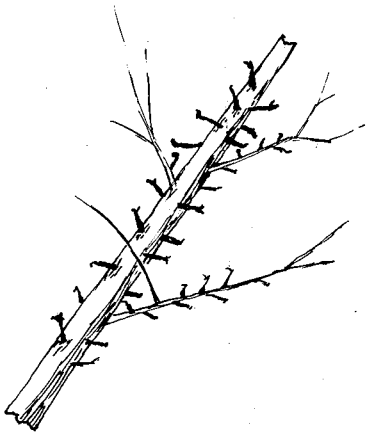
INVENTOR
Elon J. Gilbert
By Orville M. Kile
Plant Patent Agent United States Patent Office Plant Pat. 1,822
Patented Mar. 24, 1959

1,822

APPLE TREES

Elon J. Gilbert, Yakima, Wash., assignor to Columbia & Okanogan Nursery Company, Wenatchee, Wash.

Application March 5, 1958, Serial No. 719,463

1 Claim. (Cl. 47—62)

My present invention relates to a new and distinct variety of apple tree discovered by me as a sport of the Starking Delicious (unpatented) in my orchards located near Parker, Washington.

The new variety is of semi-dwarf growth which makes it possible to plant at shorter distances than can be done with its parent variety. The tree differs not only in size but in the outstanding spurred condition of its branches, it having a much greater number of fruit spurs per unit length of wood than on the parent variety and most other varieties. Its bright red coloring is a uniform over-all blush instead of the striped color pattern of the Starking Delicious. Fruit colors earlier in the season and tree bears at an earlier age than trees of the parent variety.

I have asexually reproduced my new variety in my orchards near Parker, Washington, by means of buds and grafts, and its outstanding characteristics appear to be permanent.

Accompanying illustrations show in approximately true colors, both the outside and cross-section of a specimen of this new variety, together with a small black-and-white diagrammatic illustration of a spurred branch. It is to be understood that in the taking of the color pictures, shadows indicate the blossom end of the apple to be darker than it actually is in its natural state.

In the detailed description, color plate references indicate Ridgway's Color Standards and Nomenclature, whereas mention of other colors indicates the ordinary dictionary meaning.

Tree:

*Size.*—Medium; semi-dwarf.

*Form.*—Compact. Upright in early years, becoming more spreading as large crops of fruit spread the branches.

*Trunk.*—Moderate stockiness.

*Branches.*—Medium in thickness, with many spurs.

*Color.*—Approximately Hay's Maroon (Pl. XIII).

*Leaves.*—Medium length and width; ovate with acute points; margins coarsely serrated; approximately Ivy Green (Pl. XXI).

Flowers:

*Size.*—Large.

*Color.*—Pale pink, with tinge of Carmine (Plate 1).

*Date of first bloom.*—In this climate, April 17 to 23.

*Date of full bloom.*—In this climate, May 3–9.

Fruit:

*Size.*—Uniform. Axial diameter up to 4¼ inches. Transverse diameter up to 3¾ inches.

*Shape.*—Blocky.

*Cavity.*—Symmetrical; rounded toward apex; acute; undulate; ½ inch deep by 1¼ inches broad.

*Basin.*—Symmetrical; flaring base; wide; furrowed; ⅜ inch deep by 1⅛ inches broad.

*Calyx.*—Closed; broadly lanceolate; about ¼ inch long; yellowish-green.

*Skin.*—Smooth; thick; tough; waxy appearance; color between Carmine and Oxblood (Pl. I).

*Core.*—Small; bundle area medium; base acute; halves slightly unequal.

*Flesh.*—Juicy; firm; crisp; fine-grained; rich-flavored; creamy white with slight Carmine tinge.

*Stem.*—Long; stout; brown.

*Seeds.*—Small; acute points; color Chestnut (Pl. II); shiny.

*Keeping quality.*—Excellent.

*Comparison*

The known variety most like my new variety is the Bisbee apple, subject of Plant Patent No. 1,656, the chief differences being as follows:

(1) Fruit of my new variety starts coloring later so that its finishing color is somewhat lighter and brighter.

(2) My variety tends to have a yellowish-green color in the calyx end of the fruit, whereas the Bisbee variety develops a very dark color in that area.

(3) Fruit of my variety is more blocky in shape as compared with the long and tapering shape of the Bisbee variety.

Having thus disclosed my discovery, I claim:

The new and distinct variety of apple tree, substantially as herein shown and described, characterized particularly by its semi-dwarf, upright growth; its large number of spurs per unit of stem length; the comparatively blocky form of its fruit; the early coloring of the fruit as compared with its parent; and the bright, over-all red blush type of coloring of the fruit, except for the calyx end which is yellowish-green.

References Cited in the file of this patent

UNITED STATES PATENTS

P.P. 1,565 Bisbee ..... Feb. 12, 1957